United States Patent [19]

Voigt, Jr. et al.

[11] Patent Number: 5,099,008

[45] Date of Patent: Mar. 24, 1992

[54] PROCESS OF REDUCING SHOCK SENSITIVITY OF EXPLOSIVE NITRAMINE COMPOUNDS BY CRYSTAL MODIFICATION

[75] Inventors: H. William Voigt, Jr., Stanhope; Bernard Strauss, Rockaway, both of N.J.

[73] Assignee: The United States of America as represented by the Secretary of the Army, Washington, D.C.

[21] Appl. No.: 703,305

[22] Filed: May 20, 1991

[51] Int. Cl.⁵ .................. C07D 251/06; C07D 251/02
[52] U.S. Cl. .................................. 540/475; 544/215
[58] Field of Search ................... 540/475; 544/215

[56] References Cited

U.S. PATENT DOCUMENTS 4,900,819  2/1990  Ericsson et al. ............... 540/475

*Primary Examiner*—Robert T. Bond
*Attorney, Agent, or Firm*—Anthony T. Lane; Edward Goldberg; Edward F. Costigan

[57] ABSTRACT

A process for producing very-fine crystals of a nitramine explosive selected from HMX and RDX or mixtures thereof, said crystals having a positive surface charge and being sufficiently stable to shock and to impact to meet military standards as well as having acceptable explosive power and having desirable high density. Said process comprising modifying said crystals with pyrrolidone by treating nitramine explosives selected from cyclotetramethylene tetranitramine (HMX) and cyclotrimethylene trinitramine (RDX) and mixtures thereof by (1) dissolving the nitramine in a solution of polyvinyl pyrrolidone in N-methyl-2-pyrrolidone, (2) precipitating the resulting polyvinyl pyrrolidone-modified nitramine crystals into cold water, which optionally contains the suspending agent, arabinogallactan, and in the case of HMX, beta seed crystals, (3) filtering the resulting suspension, (4) treating the resulting filter cake with a solution of polyvinyl pyrrolidone in 95% ethanol, filtering and drying the resulting filter cake at about 80° C.-90° C. to remove the ethanol and water to promote crystal density and, in the case of HMX, to convert the gamma polymorph to the denser beta polymorph and (5) recovering the resulting modified very-fine crystals of nitramine explosive.

6 Claims, No Drawings

PROCESS OF REDUCING SHOCK SENSITIVITY OF EXPLOSIVE NITRAMINE COMPOUNDS BY CRYSTAL MODIFICATION

The invention described herein may be manufactured, used and licensed by or for the Government for Governmental purposes without the payment to us of any royalties thereon.

BACKGROUND OF THE INVENTION

1. Field of Invention

This invention relates to a method of reducing the sensitivity of crystalline nitramine explosives to impact shock, fragment impact, friction and the shock of a nearby explosion. The method also renders the explosives less electrostatic when shipped or transferred during production in the dry state.

More specifically, this invention relates to the preparation of internally modified very-fine crystal nitramine explosives by a process which utilizes certain additives to internally modify such very-fine crystal nitramine explosives to render them safer than very-fine crystal nitramine explosives without such modified crystals.

2. Description of Prior Art

The crystalline nitramine explosives of military interest are (a) RDX, which may contain up to 8% HMX, and (b) beta HMX which can be used alone. HMX (octahydro-1,3,5,7-tetranitro-1,3,5,7-tetrazocine), which is a polymorph, is commonly known as cyclotetramethylene tetranitramine. Its beta polymorph has a crystal density of 1.90 grams/cc. RDX (hexahydro-1,3,5-trinitro-1,3,5-triazine), which is not polymorphic, is commonly known as cyclotrimethylene trinitramine. It has a crystal density of 1.82 grams/cc. An undesirable HMX transition polymorph (gamma) of 1.76 grams/cc crystal density can occur when HMX is undergoing crystallization.

The HMX and RDX nitramine explosives are of particular interest as very-fine crystals, e.g. about 2 to 10 microns diameter, for use in propellant and warhead formulas. Although the very-fine crystals of HMX and RDX explosives are less sensitive to friction and more uniform than larger crystals of the nitramines, such very-fine crystals have a very large active surface which is negatively charged. This negative surface charge causes a serious electrostatic safety problem when the nitramine explosives are handled in a dry state. Thus, for example, accidental explosions in plant production can occur during handling of the very-fine crystal nitramine explosives in the raw, neat state.

Previously, we found that, by thinly coating the fine nitramine crystals with, e.g. about 0.05 to 0.2% by weight polyvinyl pyrrolidone (PVP) as a complexing agent, the electrostatic handling problem is greatly diminished. An electrometer with a static tube detector shows that the PVP-treated very-fine crystal nitramine, in bulk, has a slightly positive charge. However, the impact shock sensitivity of the crystals is only marginally reduced by this state-of-art coating. Far less sensitivity is required of nitramine explosives to be used in loaded explosive and propellant containers. This is because of the threat of explosions which could result from incoming hot fragments, impact, and from sympathetic detonation. The main safety threat is to soldiers in tanks or vehicles with stored munitions.

There is clearly a need for safer very-fine crystal nitramine explosives.

SUMMARY OF INVENTION

It is therefore an object of this invention to provide slightly modified, very-fine crystals of HMX or RDX explosive having improved shock resistance relative to safety.

Another object is to provide a method for treating very-fine crystals of nitramine explosives by partial chemical complexing with the pyrrolidone group during precipitation of the very-fine crystals from a solution of N-methyl-2-pyrrolidone (NMP).

Yet another object is to provide a process to insert into the fine HMX crystal during its transformation from the low density gamma polymorph to the desired beta polymorph crystal a small amount of the more durable polyvinyl pyrrolidone (PVP) which, because it is attracted to the very-fine crystals, is both adsorbed, i.e. coated to the surface thereof, and absorbed, i.e. internally modifying the very-fine crystals.

Other objects and variations of this invention will become obvious to the skilled artisan from a reading of the following detailed specification.

DETAILED DESCRIPTION

It is known that HMX forms a complex with the pyrrolidone group, and that, similarly, RDX appears to form a somewhat weaker complex. In order to prepare a high crystal density of the nitramine explosives, preferably HMX, 0.05 to 0.5% by weight of the pyrrolidone group complexing agent, based on the weight of the crystals, is used to partially complex with and modify the crystals.

This invention provides a process for preparing PVP-modified high crystal density very-fine crystal nitramine explosives of the preferred particle size of about 2 to 5 microns which involves precipitation of the nitramine dissolved in N-methyl-2-pyrrolidone (NMP) into cold water to form fine crystals which are then slightly modified by the pyrrolidone group. The precipitate is filtered, washed with cold water and 95% ethanol, filtered again and dried. In the case of the fine modified HMX, NMP is evident in the crystal structure based on mass spectrometry analysis. The modified HMX at this point is the gamma polymorph, a crystal of undesirably low density, 1.6 g/cc, as compared to the desired beta polymorph of 1.90 g/cc density needed for the most useful explosive output. Although the density of the gamma crystals produced is insufficient to result in required explosive output, the crystal modification by the pyrrolidone causes the impact shock sensitivity to decrease, i.e. based on the results using the Navy Ordnance Lab ERL Type 12 impact test, the modified HMX has a drop weight of 85 cm height compared to about 15 cm for unmodified HMX. The modified gamma HMX can be pressed into pellets of 1.507–1.519 g/cc pressed density. By means of the process of this invention a PVP modified beta HMX having a 9% density improvement in comparable pellets of 1.609–1.621 g/cc pressed density are produced.

The process of this invention also provides a means to make a shock resistant, fine, uniform HMX slightly modified with the pyrrolidone group, and having the high density beta crystal polymorph (1.90 g/cc).

As detailed in Example 1, the process for making a PVP-modified very-fine crystal beta HMX complex comprises (1) dissolving HMX in a solution of PVP in NMP at an elevated temperature of about 80° C.–85° C. so there is about 0.1% PVP (based on HMX content)

present in the solution. The pour temperature of the solution is about 74° C. (2) precipitating the PVP-modified HMX from the solution into cold water at about 3° C. in which is suspended about 8% of a PVP-modified precipitated very-fine crystal beta HMX, as a seeding material, and preferably arabinogallactan suspending agent, (3) filtering at about 11° C. and (4) post treating the resulting filter cake which is at about 11° C. with a solution of about 0.25% to 0.50% PVP (based on HMX content) in 95% ethanol then filtering and placing the filter cake in a steam bath or oven or other heating means at about 80° C. to 90° C. to remove the ethanol.

The arabinogallactan, supplied by Champion International Company as STRactan 2, is only soluble in cold water. It is used to suspend the fine beta HMX seed and to prevent segregation of the fine pyrrolidone-complexed HMX precipitate as it forms. As the stream of hot NMP solution of HMX from step 1 contacts the cold water in step 2, very-fine crystals are formed which are attracted to the nuclei of the very-fine beta crystals of HMX seeding material. The result is that the preferred beta polymorph begins to form in the precipitation slurry of step 3. At this point there is a mixture of gamma and beta polymorph crystals.

It is necessary to avoid hot water for the precipitation and for washing the precipitate-filter cakes, to retain the slight complexing of the HMX by the pyrrolidone group.

For durability of the pyrrolidone-complexed HMX, the modification should be via the polymer, polyvinyl pyrrolidone, rather than via the solvent, NMP. In step 4, which is the key post treatment process used to convey PVP to the very-fine crystals of the filter cake produced in step 3. PVP 0.25% (based on HMX content) is dissolved in 95% ethanol and used to wash the filter cake. Unexpectedly, the PVP is selectively removed from the solution by absorption (internally) and adsorption (coating) by the PVP-complexed crystals of the filter cake. The cake is then filtered to a damp-dry condition.

To assure final conversion of all crystals to the desired beta polymorph, the damp-dry cake from step 4 is immediately heated in an enclosed container in a steam bath or in a steam oven at about 80° C.-90° C. If vacuum drying is used, the temperature for drying may be about 60° C. for 3 hours. This removes all the alcohol and assures that the crystals remain very-fine, about 2-5 micron diameter.

The process of this invention is advantageous compared to the alternative method of conversion of all the HMX to the beta polymorph by lengthy hot water digestion of the filter cake which results in excessive crystal growth.

In following this process, the initial very-fine crystal HMX seeding material of step 2 consists initially of a pure crystalline beta HMX of about 5 micron size. The resulting PVP-modified precipitated HMX end product is itself used as the seeding material in succeeding batches. These succeeding batches have the desired impact shock resistance (45-60 cm height of a drop weight for a 50% explosions impact test).

As detailed Example 2, the process for making very-fine crystal PVP-modified RDX comprises (1) dissolving RDX, preferably 7 micron size, at about 60° C. in a solution of sufficient PVP in NMP to provide 0.1% PVP (based on RDX content). The pour temperature of the solution is 60° C., (2) precipitating the treated RDX from the solution into agitated cold water (without seeding) at about 3° C. preferably containing arabinogallactan as a suspending agent, (3) filtering the resulting slurry which is about 18°-19° C. and washing with cold water, (4) washing the resulting filter cake with 95% ethanol and filtering to a damp dry condition, and (5) drying at about 80° C., removing the ethanol. The resulting dry product is non-electrostatic, and of 0.6 to 2 microns crystal size. The product has a favorable impact shock resistance of 38 cm drop height. Previously used ground RDX is electrostatic, of 7 microns crystal size, and has an impact test value of 23 cm drop height.

The following Examples illustrate the invention.

EXAMPLE 1

Very-fine PVP-modified beta HMX crystals (0.2-0.4% PVP) (54 gram preparation).

(a) In a stainless steel beaker, dissolve, by flaking 0.05 g PVP, K-90 grade (GAF Corp.) into 136 mL N-methyl-2-pyrrolidone (NMP) solvent. At 80°-85° C., dissolve (with rapid agitation) 50 g of HMX (<44 micron size preferred). Pour temperature is about 74° C.

(b) In a stainless steel beaker, prepare a solution of 0.45 g of arabinogallactan, STRactan-2 supplied by Champion International Co., in 680 mL deionized water at about 3° C. For the initial batch, suspend in this solution 4 g 5 micron beta HMX as seeding material. For the succeeding final batch suspend in this solution 4 g of the product of the initial batch, a PVP-modified precipitated beta HMX as the seeding material.

(c) In a steady stream pour the hot HMX solution of (a) into the rapidly stirred water suspension of (b) to form a precipitation slurry at a temperature of about 19° C.-21° C.

(d) Filter, using a Buchner funnel. Wash the filter cake with cold water (4° C.) washings totaling 250 mL. The filter cake temperature is about 11° C.

(e) The post-treatment to convey PVP into the very-fine crystals is as follows: Pour a solution of 0.125 to 0.25 g PVP dissolved in 95% ethanol through the filter cake of (d) twice.

(f) Filter, heat to remove the alcohol by placing the resulting damp-dry alcoholic filter cake in a stainless steel beaker in a steam bath or in a steam oven at 80° C.-90° C.

(g) The final product which is frangible and non-electrostatic, may be sieved through a US 70 sieve, is placed in a ceramic tray on a steam table for final drying. Confirmation if the resulting beta polymorph of HMX is by X-ray diffraction.

EXAMPLE 2

Very-fine PVP-modified RDX crystals (0.1% PVP) (50 gram preparation)

(a) In a stainless steel beaker, dissolve 0.05 g PVP, K-90 grade, in 106 mL N-methyl-2-pyrrolidone (NMP) solvent. Dissolve therein 50 g RDX (7-micron size preferred) at 60° C., the pour temperature.

(b) In a steady stream, pour the RDX solution into the vortex of a 3° C. solution of 0.6 g arabinogallactan (STRactan-2) in 607 mL deionized water, rapidly agitated. An air-driven propeller mixer with baffling is used for mixing. The resulting precipitation slurry temperature is about 18.5° C.

(c) Filter on a Buchner funnel. Wash the filter cake with cold water (3° C.) washings totaling 250 mL.

(d) Finally, wash the filter cake with 95% ethanol washings totaling 125 mL.

(e) Remove the cake to a ceramic tray and dry in a steam oven at 80° C. for 2 hours.

We claim:

1. A process for preparing polyvinyl pyrrolidone modified, high crystal density, very-fine crystal nitramine explosives selected from cyclotetramethylene tetranitramine and cyclotrimethylene trinitramine and mixtures thereof having sufficient shock and impact resistance to meet military safety standards as well as having a positive surface charge which comprises (1) dissolving the nitramine in a solution of polyvinyl pyrrolidone in N-methyl-2-pyrrolidone, (2) precipitating the resulting polyvinyl pyrrolidone-modified nitramine crystals into cold water, (3) filtering the resulting suspension, (4) treating the resulting filter cake with a solution of polyvinyl pyrrolidone in 95% ethanol, filtering and drying the resulting filter cake at about 80° C.-90° C. to remove the ethanol and water and (5) recovering the resulting modified very-fine crystals of nitramine explosive.

2. The process defined in claim 1 wherein the nitramine explosive is cyclotetramethylene tetranitramine and in step (2) the cold water contains arabinogallactan suspending agent and a minor amount of very-fine crystal beta cyclotetramethylene tetranitramine.

3. The process defined in claim 1 wherein the nitramine explosive is cyclotrimethylene trinitramine and in step (2) the cold water contains arabinogallactan suspending agent.

4. The process defined in claim 2 wherein the product recovered is very-fine crystal beta cyclotetramethylene tetranitramine modified externally and internally by the pyrrolidone group.

5. The very-fine crystal cyclotetramethylene tetranitramine product produced by the process of claim 2.

6. The very-fine crystal cyclotrimethylene trinitramine product produced by the process of claim 3.

* * * * *